(12) United States Patent
Chin (10) Patent No.: US 9,016,853 B2
(45) Date of Patent: Apr. 28, 2015

(54) EYEWEAR HAVING A QUICK LENS RELEASE STRUCTURE

(71) Applicant: Aswan International Corp., Taipei (TW)

(72) Inventor: Meng-Hsien Chin, Taipei (TW)

(73) Assignee: Aswan International Corp., Taipei (TW)

( * ) Notice: Subject to any disclaimer, the term of this patent is extended or adjusted under 35 U.S.C. 154(b) by 87 days.

(21) Appl. No.: 13/970,118

(22) Filed: Aug. 19, 2013

(65) Prior Publication Data

US 2015/0049294 A1  Feb. 19, 2015

(51) Int. Cl.
| | |
|---|---|
| G02C 1/00 | (2006.01) |
| G02C 1/06 | (2006.01) |
| A61F 9/02 | (2006.01) |
| G02C 5/08 | (2006.01) |
| G02C 5/00 | (2006.01) |

(52) U.S. Cl.
CPC . *G02C 1/06* (2013.01); *A61F 9/025* (2013.01); *G02C 2200/08* (2013.01); *G02C 5/08* (2013.01); *G02C 5/00* (2013.01)

(58) Field of Classification Search
CPC ............ G02C 3/02; G02C 5/00; G02C 5/001; G02C 5/008; G02C 11/08; G02C 13/00; G02C 2200/06; G02C 2200/08
USPC ......... 351/41, 44, 83, 86, 140, 149, 151, 154; 2/427, 429, 439
See application file for complete search history.

(56) References Cited

U.S. PATENT DOCUMENTS

2013/0083285 A1*  4/2013  McNeal et al. ................... 2/439

* cited by examiner

*Primary Examiner* — Huy K Mai
(74) *Attorney, Agent, or Firm* — Li&Cai Intellectual Property (USA) Office (57) ABSTRACT

An eyewear having a quick lens release structure includes a frame, a latching member, an elastic member, and a lens. The frame has a groove including a plurality of slots and a notch. The latching member is disposed in the groove and includes a lever disposed in the notch and a plurality of hooking portions disposed in the slots with portions protruding from slots. The lens is engaged to the frame and has a plurality of hooking portions. One end of the elastic member presses against the latching member, and the other end presses against the groove such that the hooking portions of the latching member and the lens can be coupled and decoupled.

10 Claims, 13 Drawing Sheets

EYEWEAR HAVING A QUICK LENS RELEASE STRUCTURE

BACKGROUND OF THE INVENTION

1. Field of the Invention

The instant disclosure relates to an eyewear; in particular, to an eyewear having a quick lens release structure.

2. Description of Related Art

As the general public becomes more interested in leisure activities such as motor-biking, surfing, skiing, etc, safety is also becoming a bigger concern. Specifically, eye protection is an important aspect of safety. As a result, sport goggles or eyewear are often used for eye protection.

Users who use regular glasses might be affected visually by scratches caused by particles after an extended period of use, and it might further affect the safety of the user while playing sports. Consequently, users tend to replace the lens periodically to ensure clear vision and eye protection. Most of the conventional lens and frame are assembled with screws respectively fixing the lens onto the frame. However, not only are the assembly and disassembly time consuming, they also require small screws which can be easily misplaced, thus rendering the assembly and disassembly inconvenient.

To address the above issues, the inventor strives via associated experience and research to present the instant disclosure, which can effectively improve the limitation described above.

SUMMARY OF THE INVENTION

The object of the instant disclosure is to provide an eyewear having a quick lens release structure which provides a quick release between the lens and the eyewear through the design of a latching member and the corresponding grooves of the frame.

In order to achieve the aforementioned objects, according to an embodiment of the instant disclosure, an eyewear having a quick lens release structure includes a frame, a latching member, an elastic member, and a lens. The frame has portions defining a groove arranged on a lateral side of the frame and a plurality of slots arranged adjacent to the groove. The slots are in air communicable with the groove. A notch is arranged adjacent to the groove and opposite the plurality of slots. A latching member is disposed in the groove. The latching member includes a plurality of spaced apart hooking portions which is arranged on a lateral side of the latching member. Each hooking portion is correspondingly disposed in each slot, and each hooking portion has a portion protruding from each slot. A lever is arranged on the other lateral side of the latching member and is movably disposed in the notch. An elastic member is disposed in the groove, one end of the elastic member presses against the latching member, and the other end of the elastic member presses against the groove. A lens is engaged to the frame, one lateral side of the lens has a plurality of hooking portions, and each hooking portion of the lens is coupled to each hooking portion of the latching member protruding from the slot. When the latching member is disposed in the groove, the elastic member presses against the latching member such that each hooking portion of the latching member is coupled to each hooking portion of the lens, the lever of the latching member is disposed on a side of the notch, and when the lever is pushed to the other side of the notch, each hooking portion of the lens are decoupled from each hooking portion of the latching member.

Moreover, the eyewear further includes two plate covers. Each plate cover includes two coupling members. Each coupling member passes through a coupling slot, defined on portions of the frame, corresponding to the coupling member. Each plate cover has a protrusion arranged on an inner wall thereon correspondingly mated to the groove and the notch. Another plate cover has a fixing portion arranged on an inner wall thereon. The lens has a fixing slot through which the lens can be coupled to the fixing portion of the plate cover.

The instant disclosure provides the following improvements. Users may be able to quickly, freehandedly, and conveniently replace the lens of the eyewear without any tools.

In order to further understand the instant disclosure, the following embodiments and illustrations are provided. However, the detailed description and drawings are merely illustrative of the disclosure, rather than limiting the scope being defined by the appended claims and equivalents thereof.

DETAILED DESCRIPTION OF THE PREFERRED EMBODIMENTS

First Embodiment

Figure 1:
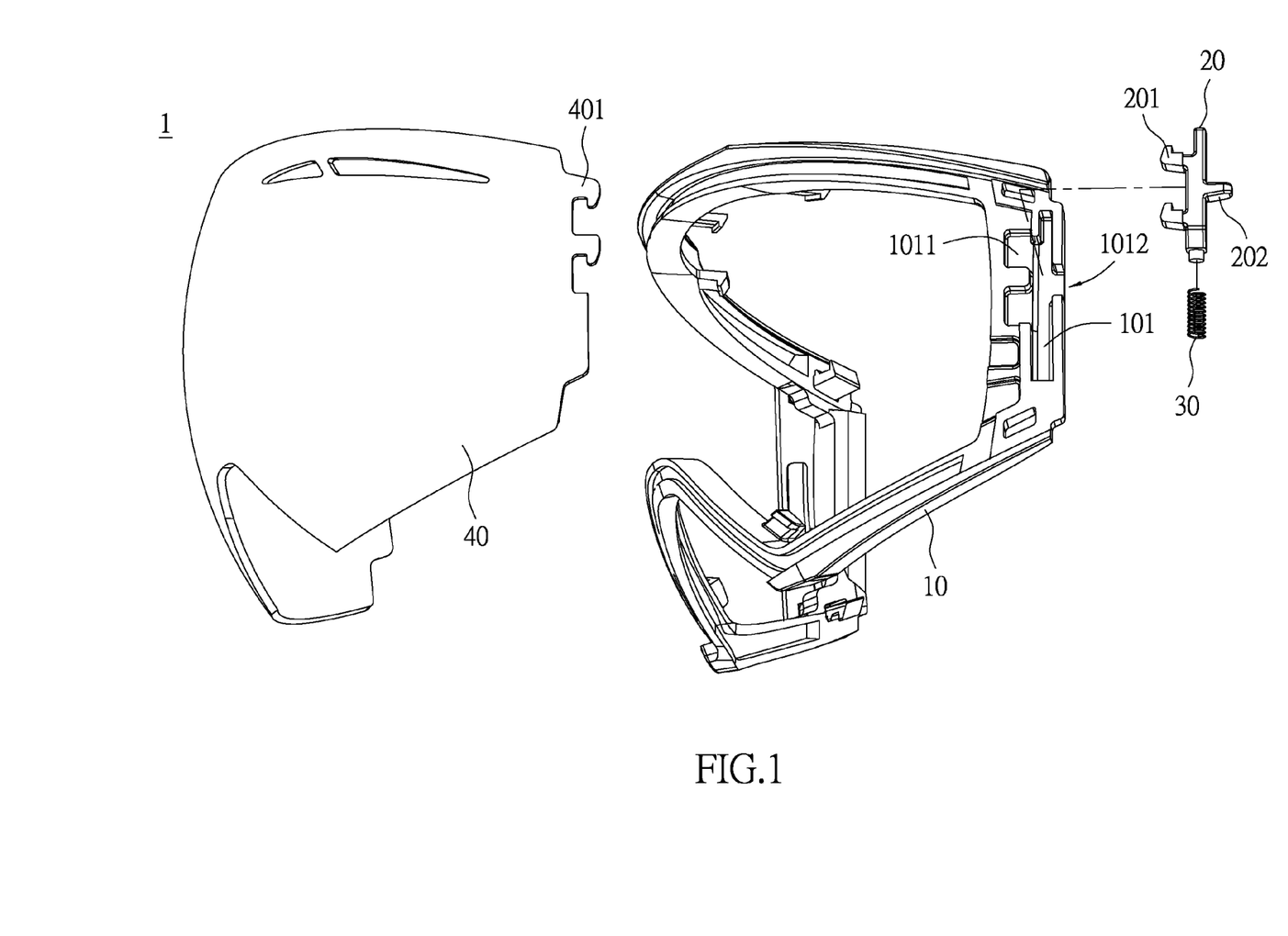
FIG. 1 is an exploded view of an eyewear having a quick lens release structure in accordance with a first embodiment of the instant disclosure.
Figure 2:
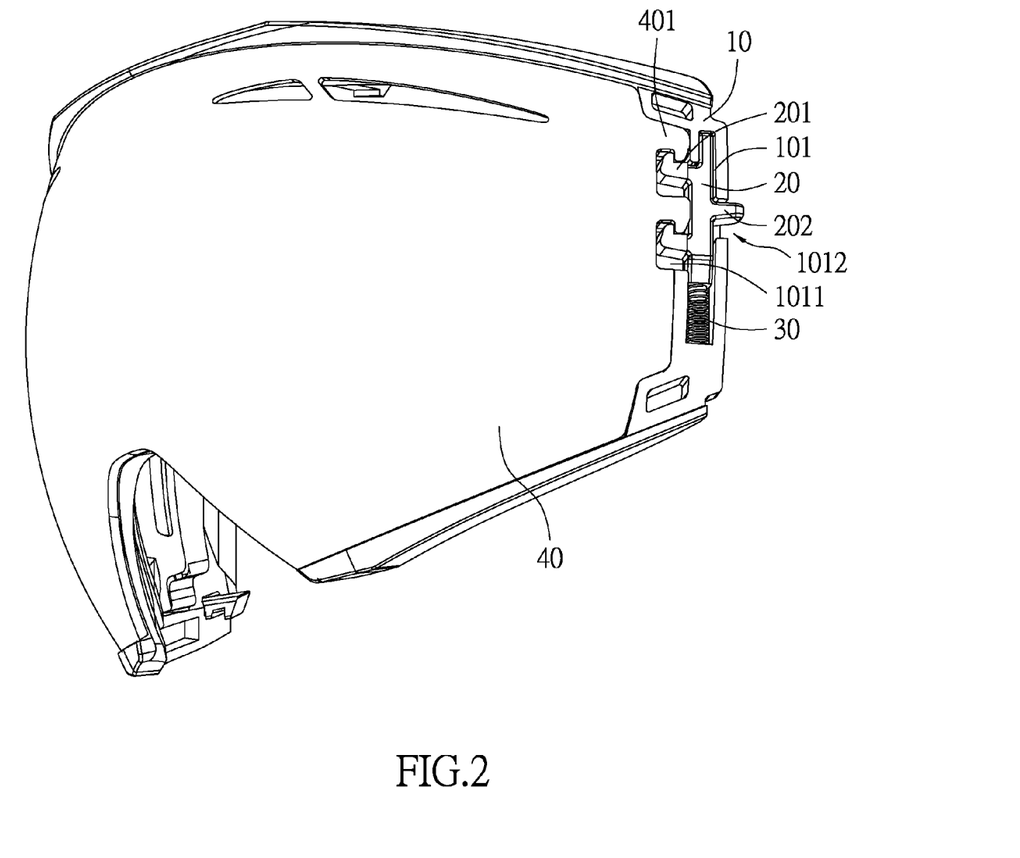
FIG. 2 is an assembled view of the eyewear having a quick lens release structure in accordance with the first embodiment of the instant disclosure.

Please refer to FIGS. 1 to 2. FIG. 1 is an exploded view of an eyewear having a quick lens release structure in accordance with a first embodiment of the instant disclosure. FIG. 2 is an assembled view of the eyewear having a quick lens release structure in accordance with the first embodiment of the instant disclosure. As shown in FIG. 1, the eyewear includes a frame 10, a latching member 20, an elastic member 30, and a lens 40. One lateral side of the frame 10 has a groove 101. The groove 101 has a plurality of slots 1011 which are arranged adjacent to the groove 101 and spaced apart from each other. The groove 101 also has a notch 1012 arranged adjacent to the groove 101 and opposite to the plurality of slots 1011. The groove 101, each slot 1011, and the notch 1012 are air communicable to each other, and are preferably formed simultaneously. A lateral side of the latching member 20 has a plurality of hooking portions 201, and the other lateral side of the latching member 20 has a lever 202. Preferably, the plurality of hooking portions 201 and the lever 202 are integrally formed, but the two components can also be formed through assembly according to specific design needs. Thus, the examples provided do not intend to limit the instant disclosure. The elastic member 30 is preferably a spring. One lateral side of the lens 40 has a plurality of hooking portions 401. Preferably, the hooking portions 401 and the lens 40 are integrally formed. Notably, the combination of the two slots 1011, two hooking portions 201 of the latching member 20, and two hooking portions 401 of the lens 40 as illustrated in FIG. 1 is one of the most preferred combinations of the instant embodiment. However, the quantity and combinations may vary according to preferences and are not limited herein. Moreover, the shapes of the hooking portions 201, 401 may also vary according to preferences and are not limited to the shapes as shown in FIG. 1. For example, the two hooking portions 201 of the latching member 20 may resemble a flipped L-shaped member, and the design of the hooking portions 401 of the lens 40 are then altered accordingly to engage to the hooking portions 201 of the latching member 20. Alternatively, the hooking portions 401 may resemble a flipped L-shaped member, and the hooking portions 201 of the latching member 20 are then altered accordingly to engage the hooking portions 401 of the lens 40. In other words, the shapes of the hooking portions 201, 401 are preferably the same but are not limited.

Figure 3:
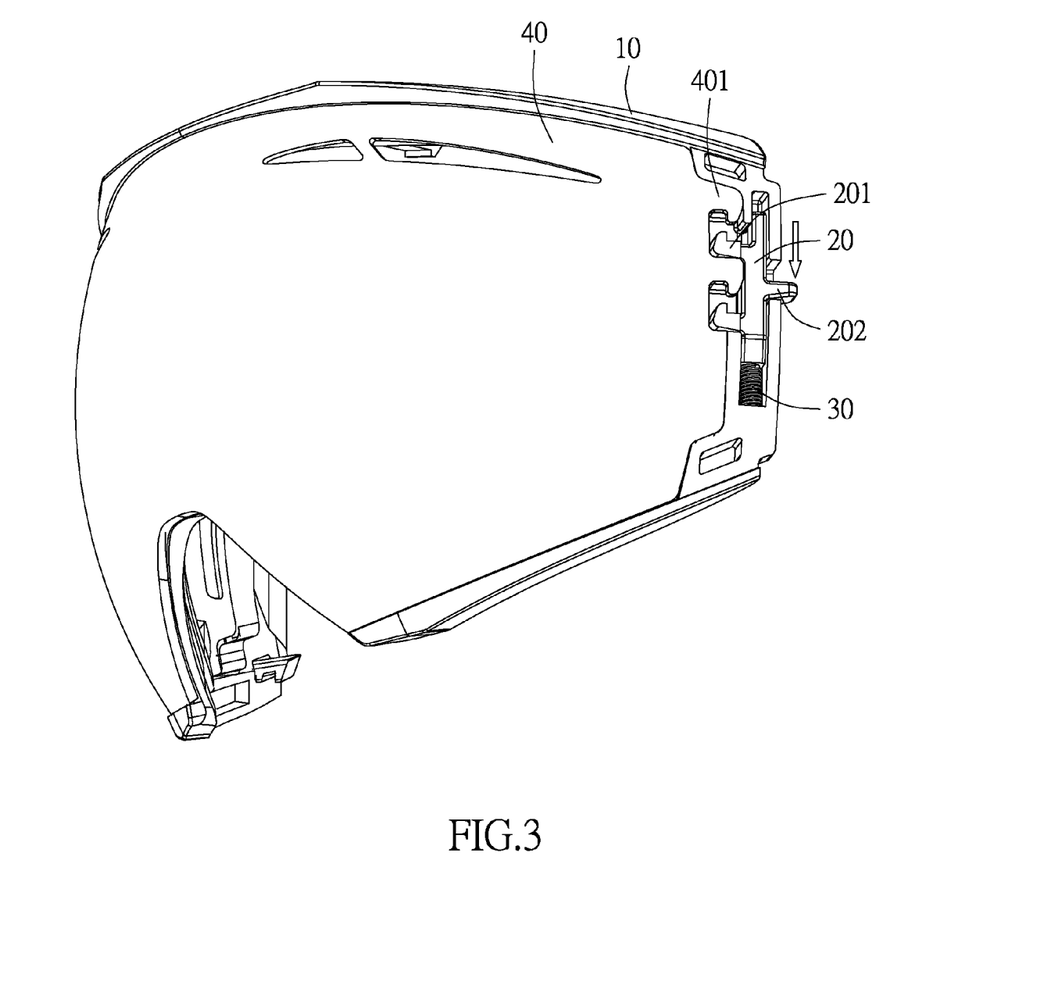
FIG. 3 is a first schematic diagram illustrating the operation of the eyewear having a quick lens release structure in accordance with the first embodiment of the instant disclosure.

As shown in FIG. 2, the latching member 20 is disposed in the groove 101, and each hooking portion 201 of the latching member 20 is correspondingly disposed in each slot 1011. The lever 202 of the latching member 20 is correspondingly disposed in the notch 2012. The elastic member 30 is disposed in the groove 101. One end of the elastic member 30 is pressed against an end (bottom end) of the latching member 20, whereas the other end of the elastic member 30 is pressed against an inner wall of the groove 101. The hooking portions 401 of the lens 40 are respectively engaged to the hooking portions 201 of the latching member 20. Notably, in the instant embodiment, if the elastic member 30 is compressed by the latching member 20, an opposite reactive force is then generated, which will press against and drive the hooking portions 201 of the latching member 20 to tightly engage the hooking portions 401 of the lens 40. Meanwhile, the lever 202 of the latching member 20 is preferably abutted against an inner wall of the notch 2012. As shown in FIG. 3, when the lever 202 of the latching member 20 is pushed against, the lever 202 is displaced from one inner wall of the notch 2012 to the other wall of the notch 2012 as the hooking portions 201 respectively displace, such that the hooking portions 201 of the latching member 20 and the hooking portions 401 of the lens 40 are disengaged. As a result, the lens 40 can be replaced.

As aforementioned, the hooking portion 201 of the latching member 20 and the hooking portion 401 of the lens 40 can provide corresponding engagement therebetween. The shapes of the hooking portions 201, 204 are not limited to the examples provided herein. Correspondingly, if the shapes of the hooking portions 201, 401 are altered, the elastic member 30 will need to be correspondingly altered. For example, if the elastic member 30 is connected to the other end of the elastic member 20, the lever 202 of the elastic member 20 is then arranged in the notch 2012 abutting the other inner wall of the notch 2012. In other words, when the lens 40 is being replaced, the direction in which the lever 202 is pushed against will be opposite from the direction as shown in previous figure. In another example, if the hooking portion 201 resembling an L-shape is engaged to the hooking portion 401 resembling the shape of a numerical number "7", the lever 202 can be pushed downwards such that the latching member 20 and the lens 40 are disengaged. Conversely, if the hooking portion 201 resembling a flipped L-shape is engaged to the hooking portion 401 resembling the shape of a flipped numerical number "7", the elastic member 30 will need to be disposed on the other end (top end) of the latching member 20 such that the lever 202 can be pushed upwards to disengage the two hooking portions 201, 401 from one another.

Figure 4:
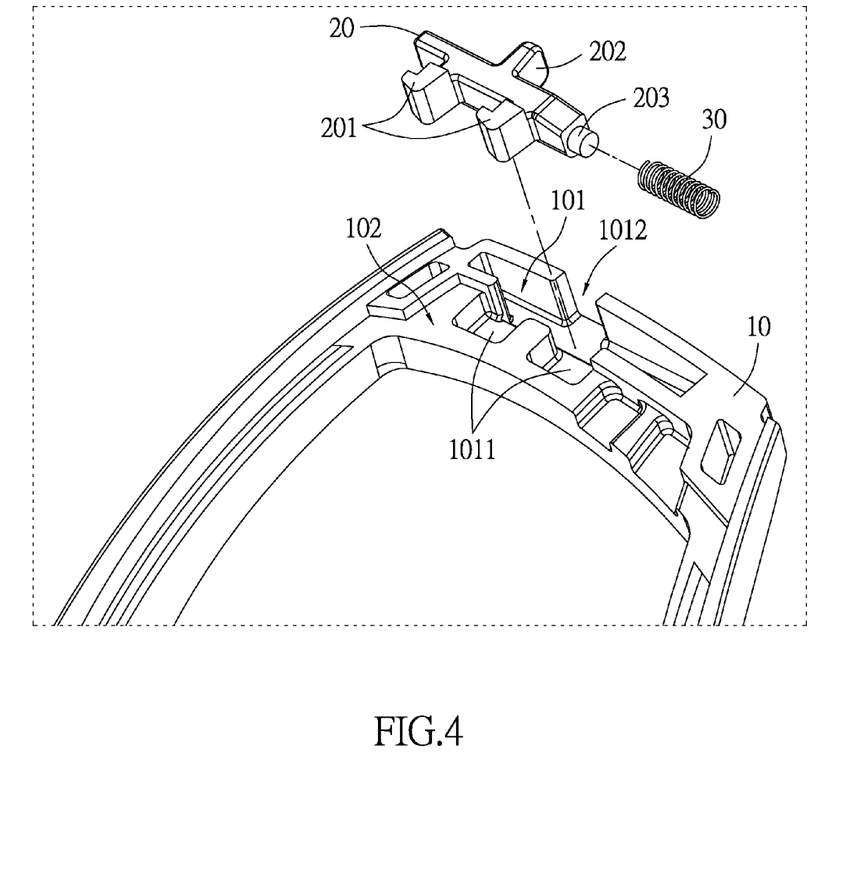
FIG. 4 is a second schematic diagram illustrating the operation of the eyewear having a quick lens release structure in accordance with the first embodiment of the instant disclosure.
Figure 5:
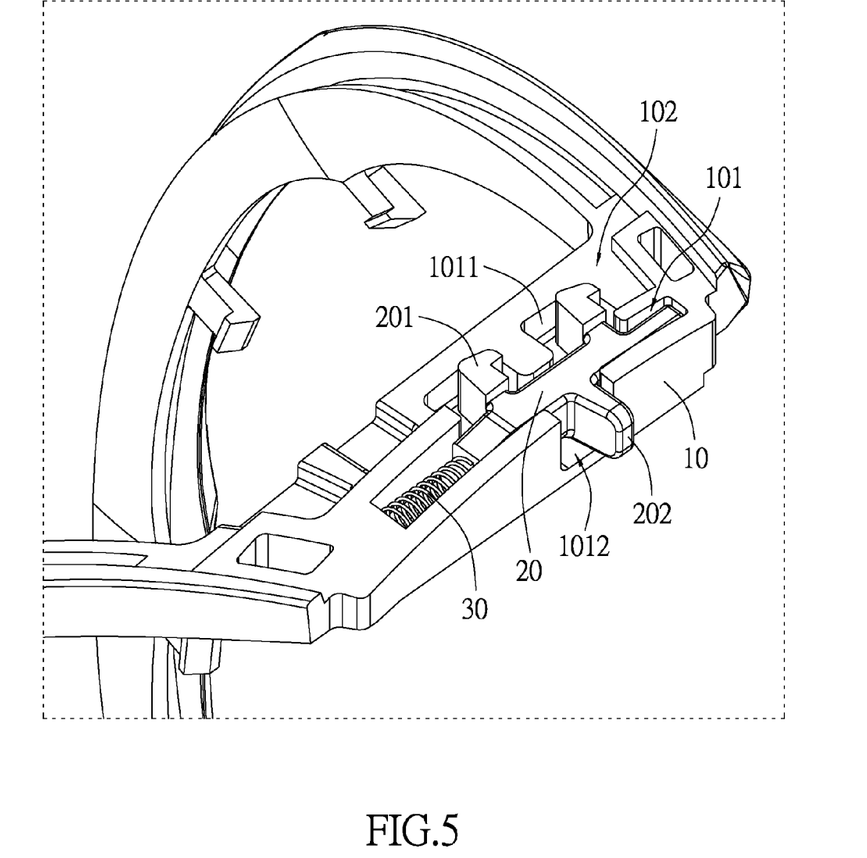
FIG. 5 is a third schematic diagram illustrating the operation of the eyewear having a quick lens release structure in accordance with the first embodiment of the instant disclosure.
Figure 6:
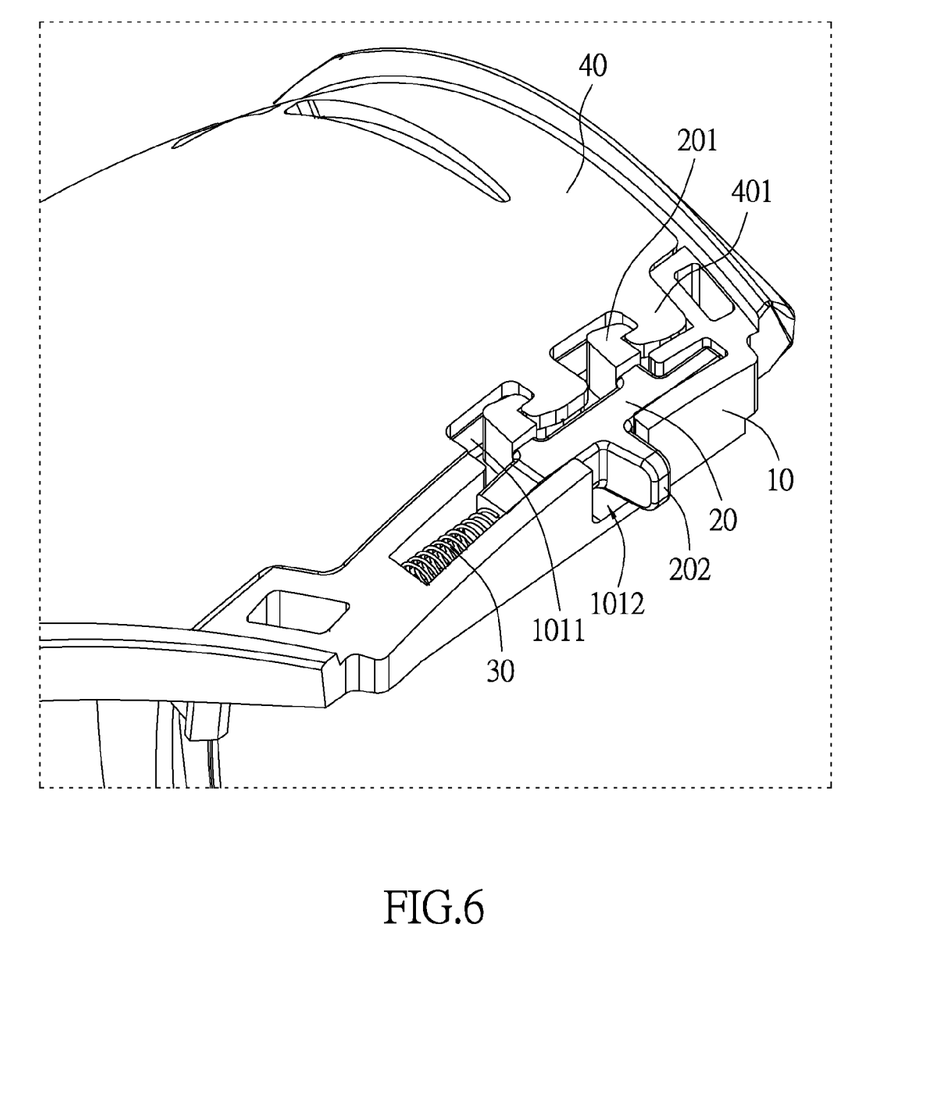
FIG. 6 is a fourth schematic diagram illustrating the operation of the eyewear having a quick lens release structure in accordance with the first embodiment of the instant disclosure.

Please refer to FIGS. 4 to 6. For description purpose, the groove 101 is viewed as a combination of a rectangular shaped groove and two slots 1011. As shown in FIGS. 4 and 5, the frame 10 further includes a lens slot 102 arranged on an inner peripheral portion of the frame 10. The lens slot 102 is also arranged adjacent to the rectangular shaped groove and above the slot 1011. The lens slot 102 is air communicable with the slot 1011. Preferably, the lens slot 102 and the slot 1011 each having a depth. The sum of the depths of the lens slot 102 and the slot 101 is substantially the same as the depth of the rectangular shaped groove. The latching member 20 further includes a knob 203 where the elastic member 30 sleeves onto. Similarly, the inner wall of the groove 101 may have a protrusion or a protruding axle arranged thereon for engaging the elastic member 30. As shown in FIG. 5, the elastic member 30 sleeves onto the knob 203 of the latching member 20. The latching member 2 and the elastic member 30 are cooperatively disposed in the groove 101, and at such time, the two hooking portions 201 of the latching member 20 each have a portion respectively protruding out of the two slots 1011. The height of the protruded portion of the hooking portions 201 is substantially the same as the depth of the lens slot 102. Then the lever 202 of the latching member 20 is correspondingly disposed in the notch 1012 of the groove 101. As shown in FIG. 6, the lens 40 is correspondingly disposed in the lens slot 102, and the hooking portions 401 of the lens 40 are respectively engaged to the hooking portions 201 of the latching member 20.

Second Embodiment

Figure 7:
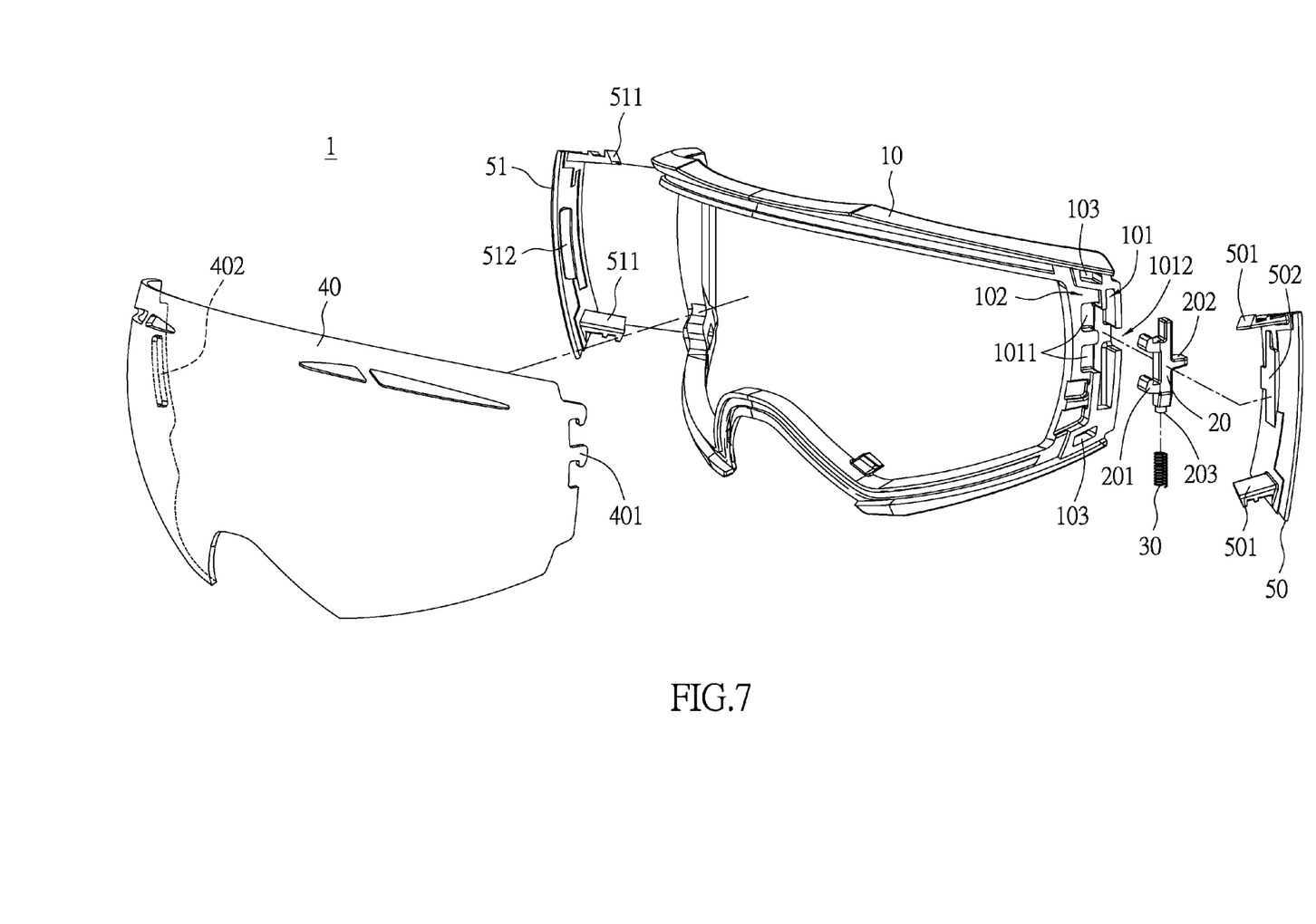
FIG. 7 is an exploded of the eyewear having a quick lens release structure in accordance with a second embodiment of the instant disclosure.
Figure 8:
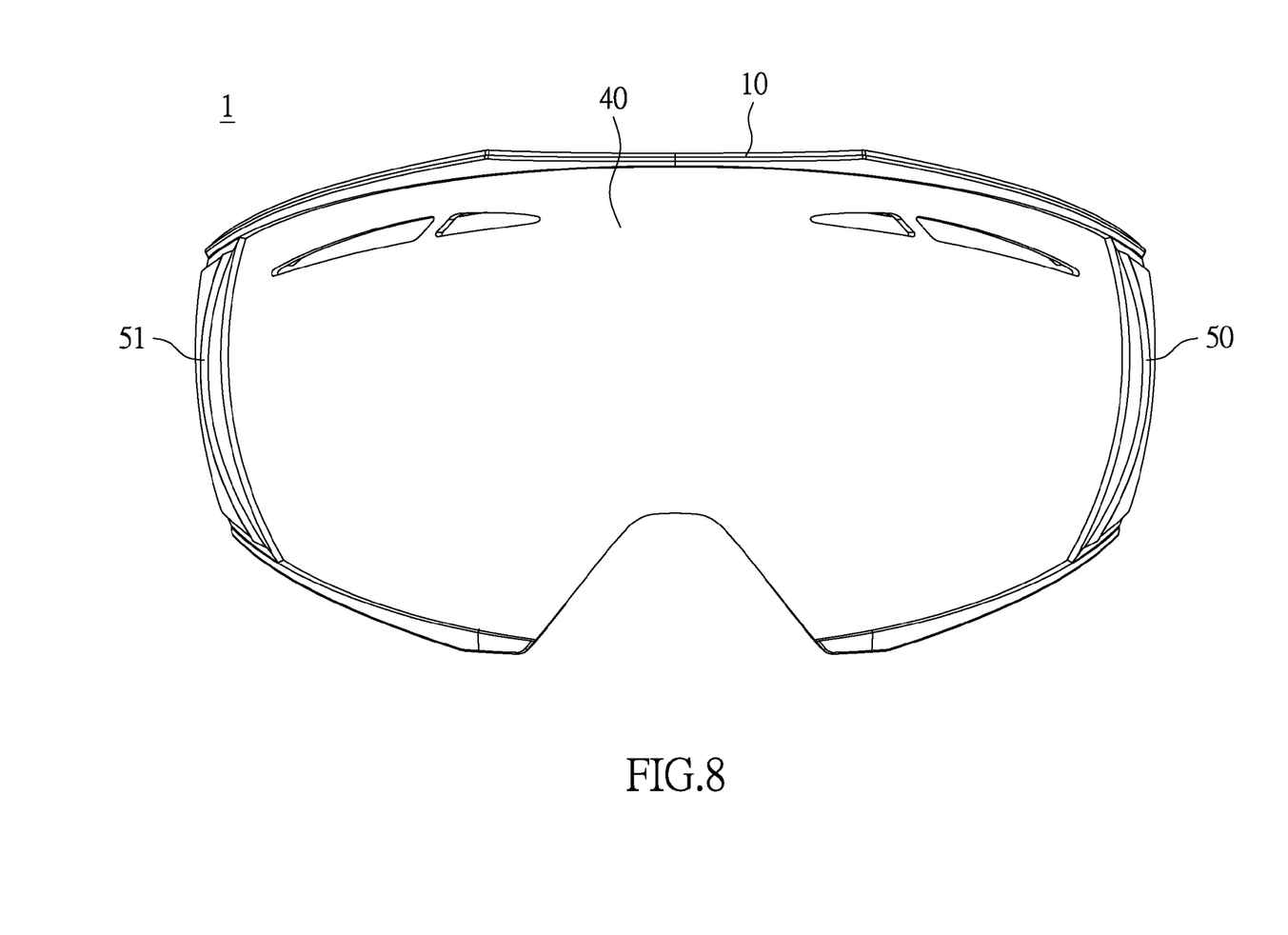
FIG. 8 is an assembled view of the eyewear having a quick lens release structure in accordance with the second embodiment of the instant disclosure.

Please refer to FIGS. 7 and 8. FIG. 7 is an exploded view of the eyewear having a quick lens release structure in accordance with a second embodiment of the instant disclosure. FIG. 8 is an assembled view of the eyewear having a quick lens release structure in accordance with the second embodiment of the instant disclosure. As shown in FIG. 7, the eyewear 1 includes the frame 10, the latching member 20, the elastic member 30, the lens 40, the right plate cover 50 and the left plate cover 51. The frame includes the groove 101, the lens slot 102, and a plurality of coupling slots 103. The plurality of coupling slots 103 are correspondingly arranged on the two lateral sides of the frame 10. As shown in figures, one coupling slot 103 is arranged on each of the top and bottom inner peripheral portions proximate to the two lateral sides of the frame 10. For example, one coupling slot 103 can be arranged proximate to four corners of the frame 10. The configuration between the groove 101, lens slot 102, the latching member 20, and the elastic member 30 are similar to the previous embodiment, and thus it is not further discussed. In the instant embodiment, two lateral sides (left and right for example) of the lens 40 respectively have the two hooking portions 401 and a fixing slot 402. The right plate cover 50 has two coupling members 501 arranged thereon, and a protrusion 502 arranged on an inner wall of the right plate cover 50. The coupling members 501 are also arranged to correspond to the positions of the coupling slots 103 of the frame 10. The left plate cover 51 has two coupling members 511 arranged thereon, and a fixing portion 512 arranged on an inner wall of the left plate cover 51. The coupling members 511 are also arranged to correspond to the positions of the coupling slots 103 of the frame 10.

Figure 9:
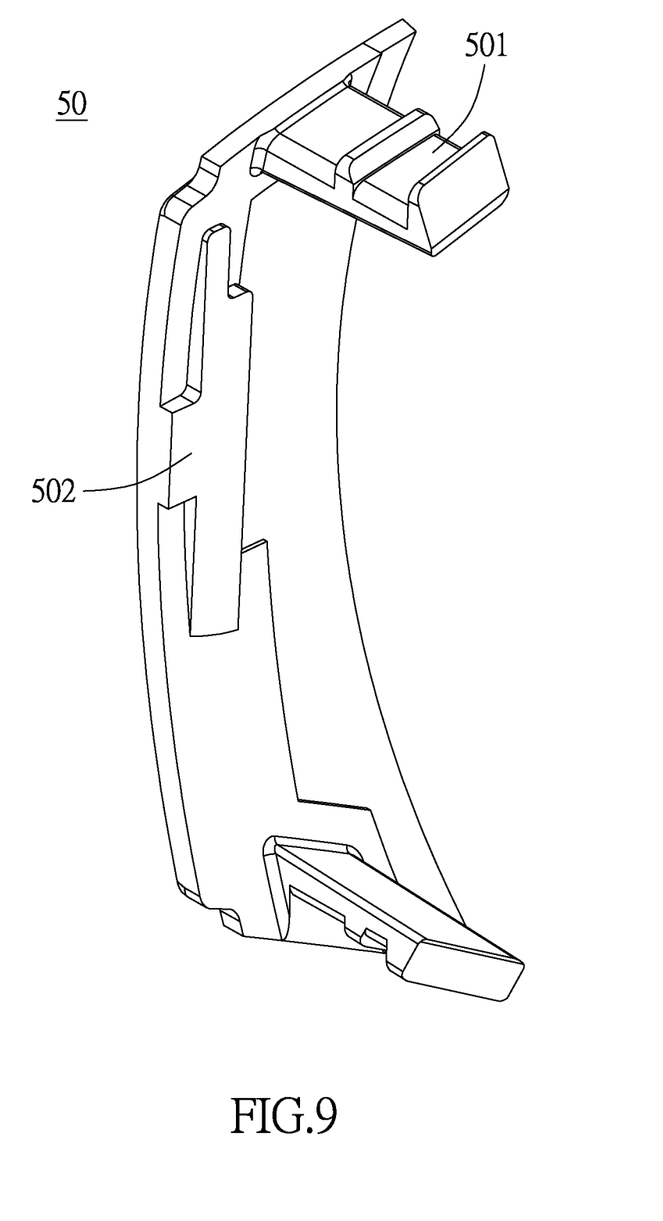
FIG. 9 is a first schematic diagram of the eyewear having a quick lens release structure in accordance with the second embodiment of the instant disclosure.

Furthermore, please refer to FIG. 9 for a schematic diagram of the right plate cover 50. A top portion and a bottom portion of the right plate cover 50 each have one coupling member 501, which can be represented as shown in FIG. 9 but not limited herein. The shape of the protrusion 502 may correspond to the shapes of the groove 101 and the notch 1012. Please refer to FIG. 6. In addition to the protruded hooking portions 201, the remaining portions of the latching member 20 has a thickness relatively smaller than a depth of the groove 101. In other words, when the latching member 20 is disposed in the groove 101, sidewalls of each hooking portion 201, sidewalls of the groove 101, sidewalls of the notch 1012, and a top surface of the latching member 20 cooperatively define a concave recess. The protrusion 502 of the right plate cover 50 has a shape which corresponds to the concave recess such that when the right plate cover 50 is installed on the frame 10, the protrusion 502 can be inserted into the concave recess and the latching member 20 can be further fixed in the groove 101.

Figure 10:
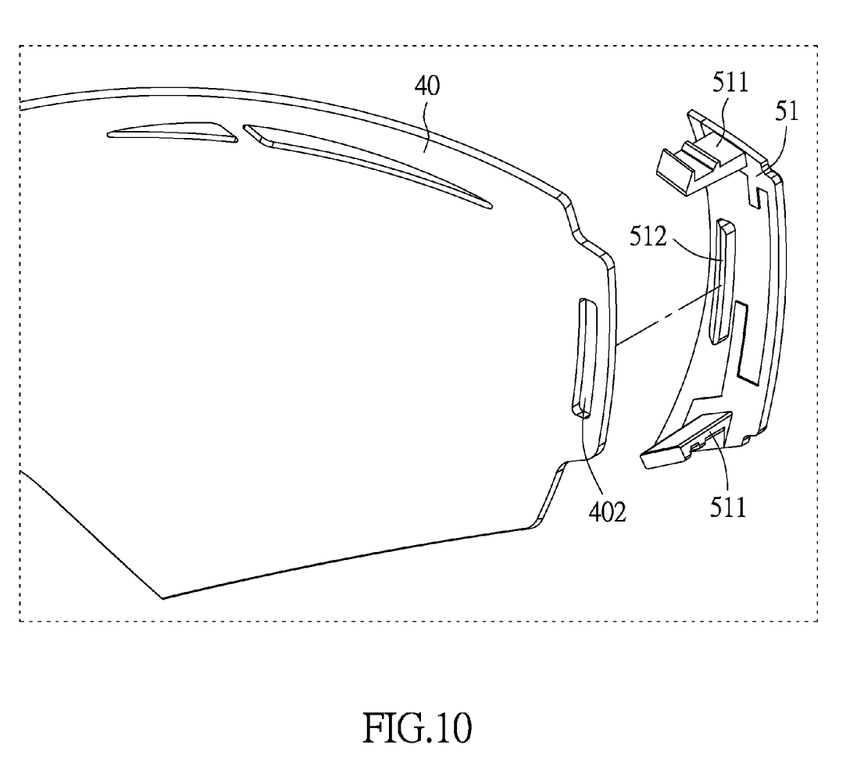
FIG. 10 is a second schematic diagram illustrating the operation of the eyewear having a quick lens release structure in accordance with the second embodiment of the instant disclosure.

FIG. 10 is a schematic diagram of the left plate cover 51. The left plate cover 51 has one fixing portion 512, one coupling member 511 arranged on a top inner surface of the plate cover 51 and another coupling member 511 arranged on a bottom inner surface of the plate cover 51. The fixing slot 402 which is arranged on one lateral side of the lens 40 can be sleeved onto the fixing portion 512 of the left plate cover 51. In another embodiment, the left plate cover 51 may have a plurality of inlaid fixing slots or openings arranged thereon. The lens 40 can also be coupled onto the plate covers 50, 51, or can form inlaid fixing slots or openings directly onto the frame 10.

Figure 11:
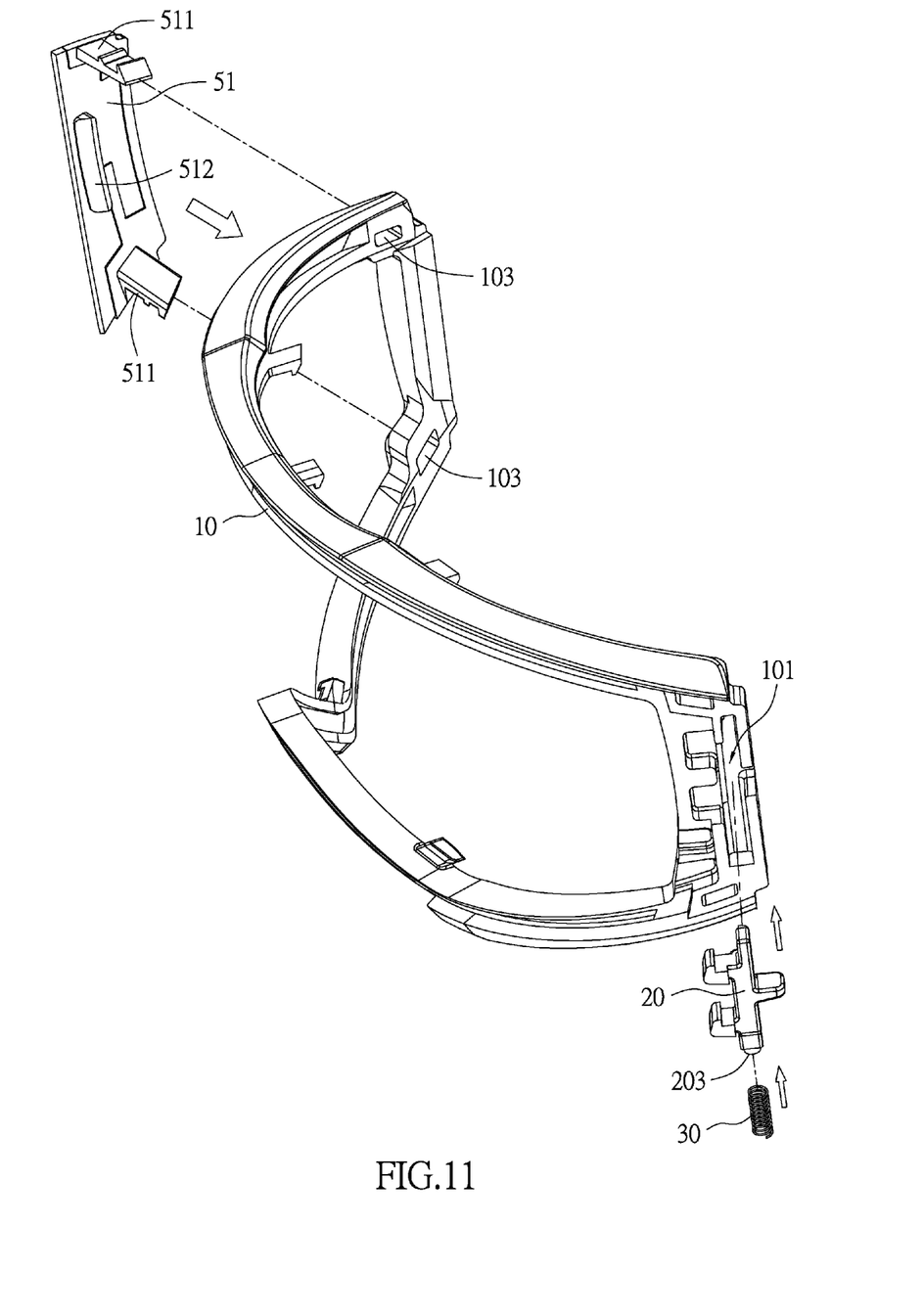
FIG. 11 is a third schematic diagram illustrating the operation of the eyewear having a quick lens release structure in accordance with the second embodiment of the instant disclosure.
Figure 12:
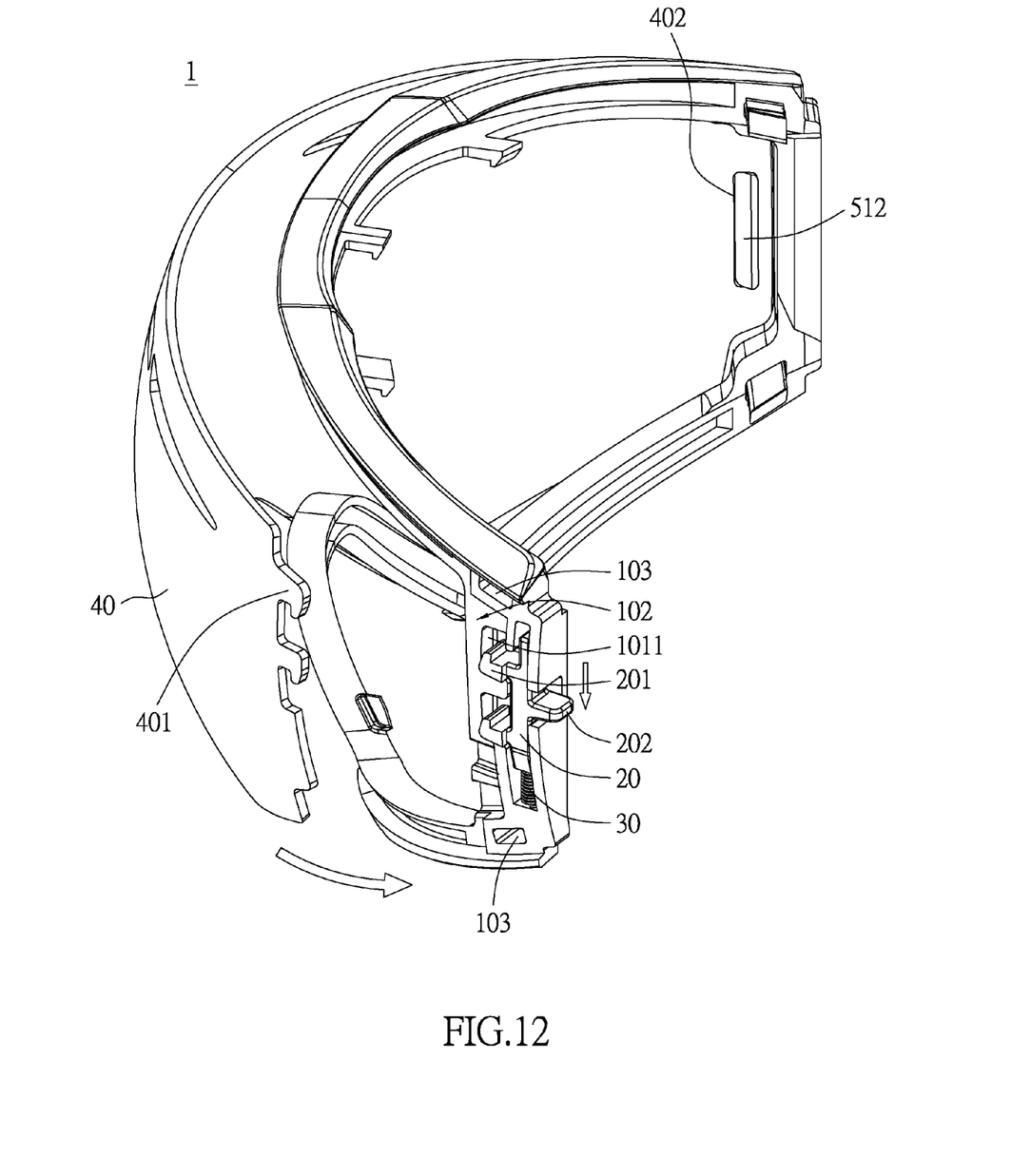
FIG. 12 is a fourth schematic diagram illustrating the operation of the eyewear having a quick lens release structure in accordance with the second embodiment of the instant disclosure.
Figure 13:
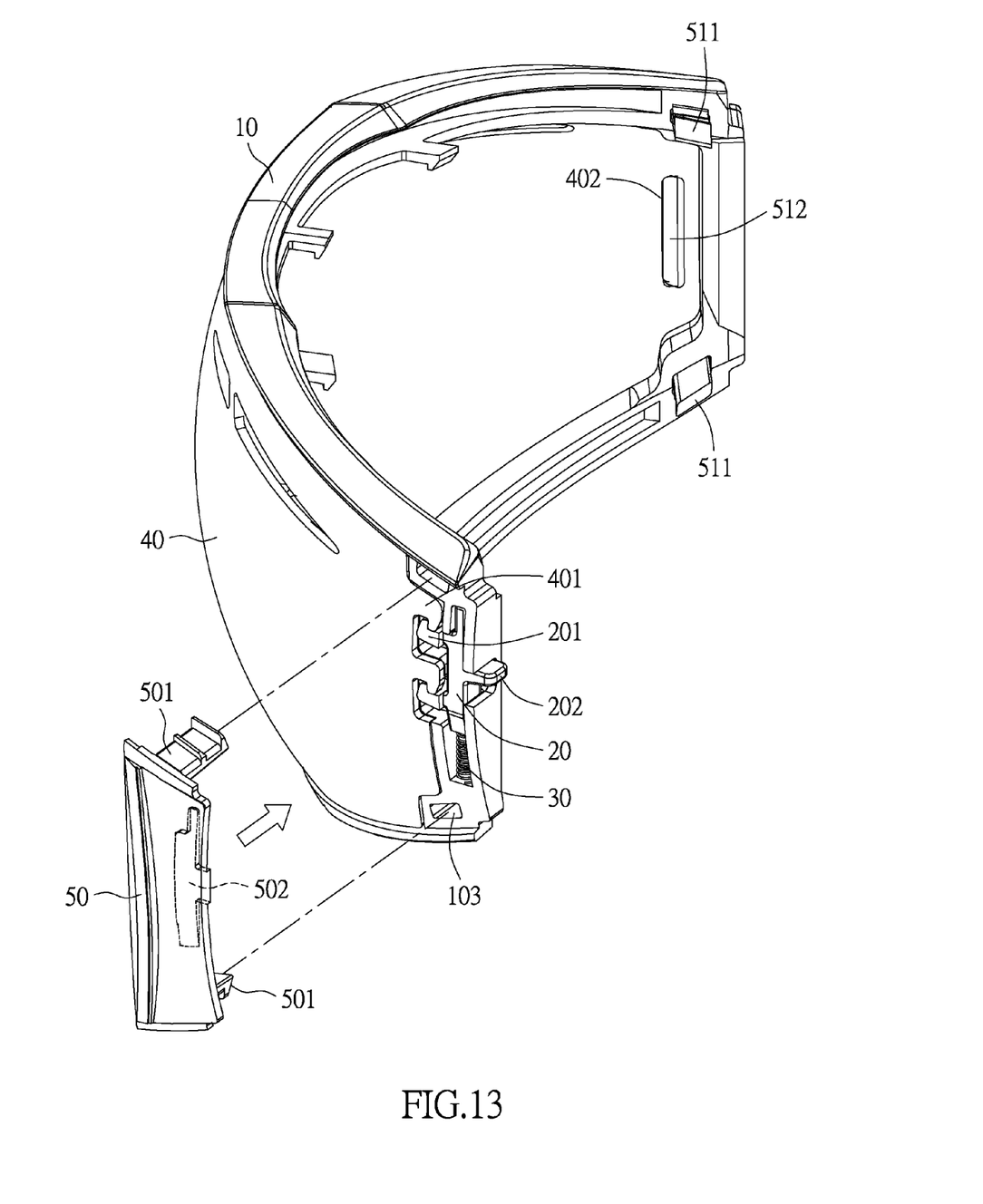
FIG. 13 is a fifth schematic diagram illustrating the operation of the eyewear having a quick lens release structure in accordance with the second embodiment of the instant disclosure.

Please refer to FIGS. 11 to 13 as the assembled view of the lens. As shown in FIG. 11, the two coupling members 511 of the left plate cover 51 respectively pass through the corresponding coupling slots 103 of the frame 10, and thus are coupled to the frame 10. Meanwhile, the elastic member 103 can be sleeved onto the knob 203 of the latching member 20 and together installed into the groove 101 of the frame 10 (please refer to FIG. 5 as the schematic diagram after the completed assembly). As shown in FIG. 12, after the left plate cover 51, the latching member 20 and the elastic member 30 have been installed, the fixing slot 402 on the left lateral side of the lens 40 correspondingly sleeves onto the fixing portion 512 of the left plate cover 51. After the left lateral side of the lens 40 is coupled to the frame 10, the lever 202 of the latching member 20 can be firstly pushed against and held in place such that each hooking portion 201 of the latching member 20 displaces downwards. Subsequently, the right lateral side of the lens 40 is correspondingly disposed in the lens slot 102 of the frame 10. Then, the lever 202 is released from hold such that the hooking portions 201 of the latching member 20 are disengaged from the hooking portions 401 of the lens 40 due to the restoration energy of the elastic member 30. Thus, the lens 40 is replaced. Lastly, the coupling members 501 of the right plate cover 50 are respectively coupled to each of the coupling slots 103 of the frame 10 to completely lens replacement.

The figures and descriptions supra set forth illustrated the preferred embodiments of the instant disclosure; however, the characteristics of the instant disclosure are by no means restricted thereto. All changes, alternations, combinations or modifications conveniently considered by those skilled in the art are deemed to be encompassed within the scope of the instant disclosure delineated by the following claims.

What is claimed is:

1. An eyewear having a quick lens release structure, comprising:
    a frame having portions defining:
        a groove arranged on a lateral side of the frame comprising:
            a plurality of slots arranged adjacent to the groove, the slots spaced apart from each other and air communicable with the groove; and
            a notch arranged adjacent to the groove and opposite the plurality of slots;
    a latching member disposed in the groove and comprising:
        a plurality of hooking portions arranged on a lateral side of the latching member, each hooking portion correspondingly disposed in each slot, and each hooking portion having a portion protruding from each slot; and
        a lever arranged on the other lateral side of the latching member and movably disposed in the notch;
    an elastic member disposed in the groove, one end of the elastic member pressing against the latching member, and the other end of the elastic member pressing against the groove; and
    a lens engaged to the frame, one lateral side of the lens having a plurality of hooking portions, and each hooking portion of the lens coupled to each hooking portion of the latching member protruding from the slot;
    wherein when the latching member is disposed in the groove, the elastic member presses against the latching member such that each hooking portion of the latching member is coupled to each hooking portion of the lens, the lever of the latching member is disposed on a side of the notch, and when the lever is pushed to the other side of the notch, each hooking portion of the lens is decoupled from each hooking portion of the latching member.

2. The eyewear having a quick lens release structure as recited in claim 1, further comprising:
    at least one plate cover engaged to the frame.

3. The eyewear having a quick lens release structure as recited in claim 2, wherein each plate cover correspondingly covers the groove, and each plate cover has a protrusion correspondingly mated to the groove and the notch.

4. The eyewear having a quick lens release structure as recited in claim 3, wherein the protrusion has a thickness corresponding to the height of the portion of the hooking portion of the latching member protruding out of the slot.

5. The eyewear having a quick lens release structure as recited in claim 2, wherein each plate cover includes at least one coupling member, and the frame has portions defining at least one coupling slot corresponding to the coupling member.

6. The eyewear having a quick lens release structure as recited in claim 2, wherein the plate cover is arranged on the other lateral side of the frame, an inner wall of the plate cover has a fixing portion, and the lens has portions defining a fixing slot corresponding to the fixing portion.

7. The eyewear having a quick lens release structure as recited in claim 1, wherein the frame further comprising:
a lens slot arranged on an inner peripheral portion of the frame.

8. The eyewear having a quick lens release structure as recited in claim 7, wherein the lens slot is arranged above and is air communicable with each slot.

9. The eyewear having a quick lens release structure as recited in claim 8, wherein the lens slot has a depth corresponding to the height of the portion of the hooking portion of the latching member protruding out of the slot.

10. The eyewear having a quick lens release structure as recited in claim 1, wherein the latching member includes a knob in which an end of the elastic member is sleeved on.

\* \* \* \* \*